United States Patent [19]

Carmona et al.

[11] Patent Number: 5,773,632

[45] Date of Patent: Jun. 30, 1998

[54] PROCESS FOR THE PREPARATION OF THE ENOL LACTONE OF 2-OXOCYCLOHEXLIDENE ACETIC ACID AND APPLICATION TO THE PREPARATION OF 2-CUOMARANONE

[75] Inventors: Nathalie Carmona; Laurent Carmona, both of Venette; Alain Perrard, Sainte Foy les Lyon; Jean-Claude Vallejos, Marseille, all of France

[73] Assignee: Clariant Chimie S.A., Puteaux, France

[21] Appl. No.: 883,594

[22] Filed: Jun. 26, 1997

[30] Foreign Application Priority Data

Jul. 9, 1996 [FR] France ................................ 96 08528

[51] Int. Cl.$^6$ .............................................. C07D 307/83
[52] U.S. Cl. .......................... 549/307; 549/462; 549/471
[58] Field of Search .................................. 549/307, 462, 549/471

[56] References Cited

U.S. PATENT DOCUMENTS 3,862,133  1/1975  Layer ..................................... 260/343.3

FOREIGN PATENT DOCUMENTS

| 2 721 609 | 12/1995 | France . |
| 1 184 774 | 1/1965 | German Dem. Rep. . |
| 0 584 372 | 9/1933 | Germany . |
| 1 337 507 | 11/1973 | United Kingdom . |

*Primary Examiner*—Ba K. Trinh
*Attorney, Agent, or Firm*—Browdy and Niemark

[57] ABSTRACT

A process for the preparation of the enol lactone of 2-oxocyclohexylidene acetic acid wherein (i) glyoxylic acid is allowed to react with cyclohexanone in the presence of a halogen acid in order to obtain a crude reaction product B1, then (ii) said crude reaction product B1 is allowed to react, after solubilisation in an organic solvent, in the presence of a strong acid soluble in said organic solvent or of strongly acid resins, in order to obtain the enol lactone of 2-oxocyclohexylidene acetic acid which is isolated if desired, and application to the preparation of 2-coumaranone.

20 Claims, No Drawings

PROCESS FOR THE PREPARATION OF THE ENOL LACTONE OF 2-OXOCYCLOHEXLIDENE ACETIC ACID AND APPLICATION TO THE PREPARATION OF 2-CUOMARANONE

The present invention relates to a process for the preparation of the enol lactone of 2-oxocyclohexylidene acetic acid and to its application to the preparation of 2-coumaranone, also called 3H-benzofuranone-2.

2-Coumaranone is a known product, widely described in the literature (cf Beil. 17, 309; I, 159; II, 331). It is the lactone of orthohydroxyphenylacetic acid and it is used as a raw material in organic synthesis for obtaining various products intended for agriculture or having physiological effects. Consequently, there is a constant search for processes by which it is possible to obtain it rapidly and cheaply from inexpensive commercial products. Surprisingly, the applicant has discovered an industrial process for the preparation of 2-coumaranone from glyoxylic acid and cyclohexanone by way of the preparation of the enol lactone of 2-oxocyclohexylidene acetic acid.

Until now, the methods of synthesis described in the literature have not permitted the industrial synthesis of 2-coumaranone. Of the syntheses found, it is possible to cite the one starting from the lactone of cis 2-hydroxy-2-acetoxy cyclohexylidene acetic acid (A. Mondon et al, Ber. 1963, 96, 826–838), the one starting from ortho-cresol (H. E. Holmquist J. Org. Chem. (1969), 34 (12), 4164–5), the one starting from trans-2-3-dichloro 2,3-dihydrobenzofuran (E. Baciocchi et al, J. Org. Chem (1979), 44(1), 32–4), the one starting from phenylacetic acid (I. Fukagawa, J. Org. Chem. (1982), 47 (12), 2491–3), and the one starting from 9,9-dichloro-7-oxabicyclo [4,3,0]nonan-8-one (N. Taichi et al, Nippon Kagaku Kaishi (1984), (8), 1287–92).

Fairly recently, J. C. Vallejos et al (FR 2.686.880) described a method for the preparation of 5-chloro-3H-benzofuranone-2 from glyoxylic acid and p-chlorophenol in the presence of phosphinic acid and catalytic quantities of iodine or hydriodic acid. They obtain a mixture of 5-chloro-3-H-benzofuranone-2 and p-chlorophenol which has to be distilled.

More recently, J. C. Vallejos et al (FR 2.721.609) described a method for the preparation of 2-coumaranone by vapour phase catalytic dehydrogenation of the crude reaction product obtained from the condensation of glyoxylic acid with cyclohexanone in a pure acetic acid medium.

This crude reaction product is composed of a mixture of trans (oxo-2-cyclohexylidene) acetic acid (hereinafter known as the trans compound), the lactone of cis (dihydroxy-2,2 cyclohexylidene) acetic acid (hereinafter known as the cis compound) and the enol lactone of 2-oxocyclohexylidene acetic acid (hereinafter known as the enol lactone compound). Catalytic dehydrogenation is carried out on a catalyst based on palladium deposited on carbon or alumina.

The three major disadvantages of the process described are the low dehydrogenation productivity, the decomposition of the products of the crude reaction product, particularly of the trans product introducing deactivation of the catalyst, dehydrogenating decarboxylation reactions of the compounds of the crude reaction product leading to the formation of orthocresol as a by-product at the beginning of the reaction.

It would be desirable, therefore, to find a process by means of which these disadvantages can be overcome.

The present invention relates to a process for the preparation of the enol lactone of 2-oxocyclohexylidene acetic acid, characterised in that (i) glyoxylic acid is allowed to react with cyclohexanone in the presence of a halogen acid in order to obtain a crude reaction product B1, then (ii) said crude reaction product B1 is allowed to react, after solubilisation in an organic solvent, in the presence of a strong acid soluble in said organic solvent or of strongly acid resins, in order to obtain the enol lactone of the expected 2-oxocyclohexylidene acetic acid which is isolated if desired.

In the first stage, glyoxylic acid is allowed to react with cyclohexanone in the presence of a halogen acid, preferably at a temperature greater than 50° C., in the presence or absence of a solvent in order to obtain a crude reaction product B1. The latter contains mainly cis compound, a little of the enol lactone compound and very little of the trans compound.

In the second stage, the crude reaction product B1 is dehydrated in order to obtain the pure enol lactone compound, if desired after isolation. This dehydration is carried out in the presence of a strong acid soluble in the organic solvent or of strongly acid resins, preferably at a temperature greater than 50° C., particularly in the presence of a benzene solvent.

The compound of the enol lactone type has been described on several occasions, Yu Wang, Hua Hsueh Hsueh Pao 26, No. 2, 84–99 (1960)—M. N. Kolosov, Zh. Obshch.Khim. 32, 2893–905 (1962)—R. W. Saalfrank, Chem. Ber. 1983, 116(4), 1463–7—T. Nakano, J. C. S., Chem. Commun., 1981, 815–816—Yu. A. Arbuzov, Zh. Obshch. Khim. 32, 3676–81 (1962)—L. Baiocchi, Synthesis 1979, 434–6—A. Mondon, Ber. 1963, 96, 826–839—M. M. Shemyakin, Doklady Akad. Nauk. SSSSR, 128, 744–7 (1959)—G. Klotmann, DE 1.955.375 (1969), but none of the references indicates a synthesis producing the pure product with a good yield and at a reasonable price, which can be transferred to an industrial scale.

Under preferential conditions of carrying out the invention, the process described above is carried out in the following manner:

In the first stage, glyoxylic acid is allowed to react with cyclohexanone:

at a temperature greater than 50° C., preferably greater than 80° C., more particularly between 100° C. and 110° C., in the presence of a halogen acid which is hydrochloric acid in a quantity of 1 to 100 mole %, preferably 10 to 25 mole % with respect to glyoxylic acid, in the presence or absence of an organic solvent or otherwise such as toluene, water, acetic acid, with a molar ratio of cyclohexanone/glyoxylic acid greater than or equal to 1, preferably between 1 and 2, and a crude reaction product B1 is obtained, containing mainly the cis compound, a little of the enol lactone compound, and very little trans compound.

In the second stage, the crude reaction product B1 is dehydrated:

at a temperature greater than 50° C., more particularly between 80° C. and 160° C., in the presence of a strong acid soluble in an organic medium (p-toluene sulphonic acid, methane sulphonic acid, . . . ) or of strongly acid resins (of the Amberlyst® type from Rohm and Haas, for example), preferably in the presence of a benzene solvent.

The process above has a very particular advantage in the preparation of 2-coumaranone, also called 3H-benzofuranone-2. Indeed, the enol lactone may be converted very easily by dehydrogenation to 2-coumaranone.

The present invention also relates, therefore, to an above process, characterised in that the enol lactone is isolated and, moreover, vapour phase catalytic dehydrogenation of the enol lactone compound is carried out in the presence of a dehydrogenation catalyst.

The term "dehydrogenation catalyst" refers to a known catalyst for the aromatisation of 6-membered rings such as those mentioned in Advanced Organic Chemistry, Jerry March, 3rd edition, pages 1052–1054, J. Wiley Interscience, New-York, 1985 and in Houben-Weyl, Phenole, Vol. 2, pages 701–716, Georg Thieme- Stuttgart, 1976.

In preference, the dehydrogenation catalyst is chosen from the group comprising palladium and platinum.

Under preferential conditions of implementation, the enol lactone compound is dehydrogenated:
- by evaporation at a temperature greater than or equal to 150° C., more particularly between 200° C. and 300° C.,
- entrained over the catalyst by means of a carrier gas composed preferably of dinitrogen,
- in the presence of a catalyst based on platinum or palladium deposited on an inert solid support such as α alumina, γ alumina, silica, silicon carbide, carbon, having a specific surface greater than 1 $m^2$ per gram, in a concentration greater than or equal to 0.5%, more particularly between 0.5 and 5%.

The gaseous mixture analysed by chromatography after condensation in traps containing acetonitrile may be distilled in order to lead to the 2-coumaranone isolated.

The originality of the object of the present patent application in comparison with the patent FR 2.721.609 of J. C. Vallejos starting from the same starting products cyclohexanone and glyoxylic acid lies in the fact that it was possible to produce the enol lactone compound isolated with a remarkable yield. This product is stable, does not decompose and does not poison the catalyst. It is liquid and does not require the use of solvent. It is readily evaporated and the reaction may be carried out with a low gas flow. A better 2-coumaranone productivity is obtained whilst retaining good stability of the catalyst over time (no catalyst poisoning) by vapour phase catalytic dehydrogenation of the enol lactone compound isolated.

The following examples illustrate the present invention yet without limiting its scope.

EXAMPLE 1

Preparation of the Enol Lactone of 2-oxocyclohexylidene Acetic Aacid

The following are introduced into a 1 liter flask:
148 g of 50% glyoxylic acid (1 mole)
147 g of cyclohexanone (1.5 mole)
74 g of water
10 g of HCl in 37% solution in water.

The solution is then refluxed for 2 hours then concentrated under a reduced pressure of 20 mm of Hg in order to remove the water, hydrochloric acid and excess cyclohexanone.

A mixture composed of 82% of cis compound, 12% of enol lactone type compound, 1.6% of trans compound is obtained, this composition having been determined by HPLC.

The mixture is then solubilised in 250 ml of xylene in the presence of 10 g of p-toluene sulphonic acid (PTSA).

The water present is then removed by azeotropic distillation with xylene.

After neutralisation, the crude mixture is then distilled under a reduced pressure of 4 mm of Hg and 118 g (0.87 mole) of enol lactone type compound are obtained (boiling point 120° C. under 4 mm Hg), i.e. a yield of 87% with respect to the initial glyoxylic acid.

EXAMPLE 2

Variant of the Preparation of the Enol Lactone of 2-oxocyclohexylidene Acetic Acid The following are introduced into a 1 liter flask:
148 g of 50% glyoxylic acid (1 mole)
196 g of cyclohexanone (2 moles)
74 g of water
25 g of HCl in 37% solution in water.

The solution is then refluxed for 2 hours, then concentrated under a reduced pressure of 20 mm of Hg in order to remove the water, hydrochloric acid and excess cyclohexanone.

A mixture composed of 77% of cis compound, 20% of enol lactone type compound, 2% of trans compound is obtained, this composition having been determined by HPLC.

The mixture is then solubilised in 250 ml of toluene in the presence of 20 g of a sulphonic resin Amberlyst®15. The water is then removed by azeotropic distillation with toluene.

After filtration, the crude mixture is then distilled under a reduced pressure of 4 mm of Hg and 122 g (0.90 mole) of enol lactone type compound are obtained (boiling point 120° C. under 4 mm of Hg), i.e. a yield of 90% with respect to the initial glyoxylic acid.

EXAMPLE 3

Obtaining 2-coumaranone from the Isolated Enol Lactone of 2-oxocyclohexylidene Acid In an evaporator kept at a temperature of 220° C., a solution S1 composed exclusively of enol lactone of 2-oxocyclohexylidene acetic acid is evaporated at a flow rate of 12 ml/h and the vapours are entrained by a stream of nitrogen at a flow rate of 200 l/h towards the reactor kept at a temperature of 250° C.

The reactor is a vertical cylinder with an internal diameter of 26 mm and a length of 200 mm, sealed at its lower end by a sintered glass, with a useful volume of 80 ml. It is packed with a catalyst of the $Pd/Al_2O_3$ type (30 g of catalyst i.e. 150 mg of Pd). At the outlet of the reactor, the hot gases are cooled and condensed by passing into traps containing acetonitrile, then analysed by high performance liquid chromatography (HPLC) and by gas chromatography (GC).

The 2-coumaranone yield and productivity are defined respectively as:
Y (coum)=(no. of moles of 2-coumaranone)/(no. of moles of reagents) expressed in %
Productivity=(mass of 2-coumaranone)/(reaction time)/(mass of palladium involved) expressed in g/h/g of Pd.
The results obtained are summarised in Table 1.

TABLE 1

Catalytic dehydrogenation of the enol lactone

| t(h) | Y(coum) | Productivity (g/h/g of Pd) |
| --- | --- | --- |
| 1 | 71 | 54 |
| 2 | 68 | 52 |
| 4 | 69 | 53 |
| 6 | 69 | 52 |
| 8 | 66 | 51 |

The use of the pure enol lactone as substrate makes it possible to obtain:
a high productivity greater than 50 g/h/g of Pd;

good stability of the catalyst used: as the starting product is stable, there is no poisoning of the catalyst;

a reaction in the absence of solvent hence the aerosol is easily trapped;

favourable experimental conditions thanks to the ease of evaporation of the product and the possibility of using small gas flows.

EXAMPLE 4

Obtaining 2-coumaranone from a Mixture Derived from the Condensation of Cyclohexanone and Glyoxylic Acid Under Conditions Similar to Those Described in Patent FR 2.721.609.

Under conditions identical to those of example 3, a solution S2 is used, containing 18.5% of cis
16.2% of trans
0.4% of enol lactone
64.9% of acetic acid.

The results obtained are summarised in Table 2.

TABLE 2

Catalytic dehydrogenation of α-carboxymethylidene cyclohexanones

| t(h) | Y(coum) | Productivity (g/h/g of Pd) |
| --- | --- | --- |
| 1 | 34 | 9 |
| 2 | 4.3 | 1.2 |

It can be seen that the 2-coumaranone yield and productivity are already very much lower at the end of 2 hours compared with the results obtained with the present process described.

In contrast, it can be ascertained that even after 8 hours' reaction with the present process, the 2-coumaranone yield and productivity are still very good (see Table 1).

We claim:

1. A process for the preparation of the enol lactone of 2-oxocyclohexylidene acetic acid, characterised in that
   (i) glyoxylic acid is allowed to react with cyclohexanone in the presence of a halogen acid in order to obtain a crude reaction product B1, then
   (ii) said crude reaction product B1 is allowed to react, after solubilisation in an organic solvent, in the presence of a strong acid soluble in said organic solvent or of strongly acid resins, in order to obtain the enol lactone of 2-oxocyclohexylidene acetic acid which is isolated if desired.

2. A process according to claim 1, characterised in that the halogen acid of stage (i) is hydrochloric acid in a quantity of 1 to 100 mole % with respect to glyoxylic acid.

3. A process according to claim 2, characterised in that stage (i) is carried out at a temperature greater than 50° C.

4. A process according to claim 3, characterised in that the organic solvent for solubilising the crude product B1 in stage (ii) is a benzene solvent.

5. A process according to claim 4, characterised in that a strong acid is used which is p-toluene sulphonic acid or methane sulphonic acid.

6. A process according to claim 4, characterised in that a strongly acid resin is used which is a sulphonic resin of the Amberlyst® type.

7. A process according to claim 5, characterised in that the enol lactone is isolated and that, moreover, vapour phase catalytic dehydrogenation of the enol lactone compound is carried out in the presence of a dehydrogenation catalyst in order to obtain 2-coumaranone.

8. A process according to claim 7, characterised in that the vapour phase reaction is carried out at a temperature greater than or equal to 150° C.

9. A process according to claim 7, characterised in that the dehydrogenation catalyst is chosen from the group comprising palladium and platinum.

10. A process according to claim 7, characterised in that the dehydrogenation catalyst is deposited on an inert solid support having a specific surface of more than 1 m²/g.

11. A process according to claim 6, characterized in that the enol lactone is isolated and that, moreover, vapor phase catalytic dehydrogenation of the enol lactone compound is carried out in the presence of a dehydrogenation catalyst in order to obtain 2-coumaranone.

12. A process according to claim 11, characterized in that the vapor phase reaction is carried out at a temperature greater than or equal to 150° C.

13. A process according to claim 12, characterized in that the dehydrogenation catalyst is chosen from the group comprising palladium and platinum.

14. A process according to claim 8, characterized in that the dehydrogenation catalyst is chosen from the group comprising palladium and platinum.

15. A process according to claim 14, characterized in that the dehydrogenation catalyst is deposited on an inert solid support having a specific surface of more than 1 m²/g.

16. A process according to claim 1, characterized in that stage (i) is carried out at a temperature greater than 50° C.

17. A process according to claim 1, characterized in that the organic solvent for solubilising the crude product B1 in stage (ii) is a benzene solvent.

18. A process according to claim 1, characterized in that a strong acid is used which is p-toluene sulphoric acid or methane sulphonic acid.

19. A process according to claim 1, characterized in that a strongly acid resin is used which is a sulphonic resin of the Amberlyst type.

20. A process according to claim 1, characterized in that the enol lactone is isolated and that, moreover, vapor phase catalytic dehydrogenation of the enol lactone compound is carried out in the presence of a dehydrogenation catalyst in order to obtain 2-coumaranone.

* * * * *